United States Patent
Murayama et al.

(10) Patent No.: US 8,963,078 B2
(45) Date of Patent: Feb. 24, 2015

(54) ION GROUP IRRADIATION DEVICE AND SECONDARY ION MASS SPECTROMETER

(71) Applicant: Canon Kabushiki Kaisha, Tokyo (JP)

(72) Inventors: Yohei Murayama, Kawasaki (JP); Kota Iwasaki, Atsugi (JP); Masafumi Kyogaku, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/307,696

(22) Filed: Jun. 18, 2014

(65) Prior Publication Data

US 2014/0374587 A1 Dec. 25, 2014

(30) Foreign Application Priority Data

Jun. 24, 2013 (JP) .................................. 2013-131637

(51) Int. Cl.
- *B01D 59/44* (2006.01)
- *H01J 49/00* (2006.01)
- *H01J 49/10* (2006.01)

(52) U.S. Cl.
CPC ....................................... *H01J 49/10* (2013.01)
USPC ........... 250/282; 250/281; 250/251; 250/288; 250/492.21

(58) Field of Classification Search
USPC ...................... 250/281, 282, 288, 251, 492.21
See application file for complete search history.

(56) References Cited

U.S. PATENT DOCUMENTS

| | | | |
|---|---|---|---|
| 6,906,323 B2 | 6/2005 | Yamada et al. | |
| 7,038,217 B2 | 5/2006 | Yamada et al. | |
| 2012/0045615 A1* | 2/2012 | Kirkpatrick et al. | 428/141 |
| 2014/0138533 A1 | 5/2014 | Iwasaki | |
| 2014/0252225 A1 | 9/2014 | Iwasaki | |

FOREIGN PATENT DOCUMENTS

| | | |
|---|---|---|
| JP | 3530942 B2 | 5/2004 |
| JP | 2011-029043 A | 2/2011 |

* cited by examiner

*Primary Examiner* — Jack Berman
*Assistant Examiner* — Meenakshi Sahu
(74) *Attorney, Agent, or Firm* — Fitzpatrick, Cella, Harper & Scinto

(57) ABSTRACT

The present invention provides an ion group irradiation device which includes: an ion source which generates an ion; and an ion group selecting unit which selects an ion group containing a cluster ion from ions released from the ion source, in an ion group irradiation device for irradiating a sample with the ion group, wherein the ion source has a pressure gradient forming unit for changing a pressure with which a material of the cluster ion is jetted, with time, the ion group selecting unit has a chopper which performs a chopping operation of selecting the ion group by passing and blocking the cluster ions in a traveling direction by the opening and closing of the chopper, and the chopper performs two or more times of the chopping operations per one time of a pressure gradient forming operation by the pressure gradient forming unit.

17 Claims, 5 Drawing Sheets

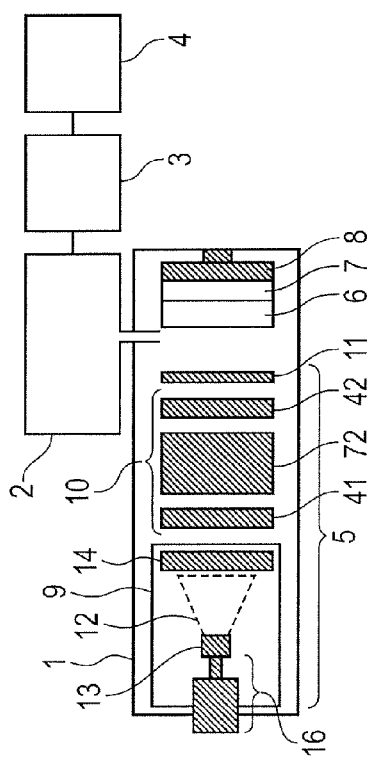
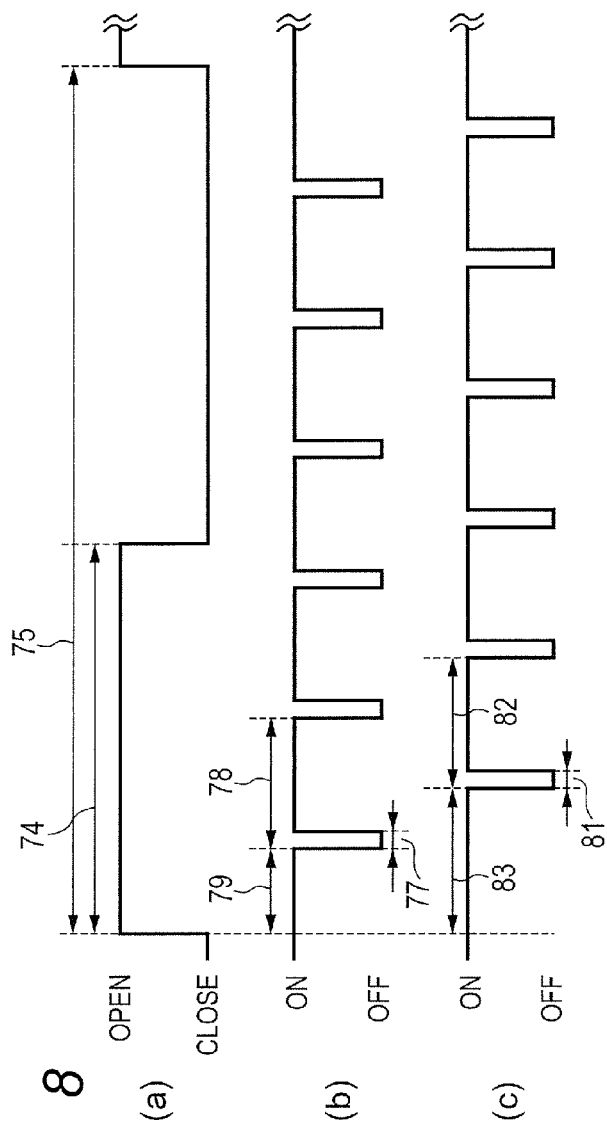
FIG. 7
FIG. 8

ION GROUP IRRADIATION DEVICE AND SECONDARY ION MASS SPECTROMETER

BACKGROUND OF THE INVENTION

1. Field of the Invention

The present invention relates to an ion group irradiation device. The present invention also relates to a secondary ion mass spectrometer which analyzes an atom and a molecule that constitute the surface of a sample.

2. Description of the Related Art

Secondary ion mass spectroscopy (SIMS: Secondary Ion Mass Spectroscopy) is an analysis method of irradiating a sample with a primary ion beam, measuring a mass-to-charge ratio of a secondary ion emitted from the surface of a sample, and thereby specifying a species of the atom or a species of the molecule that constitutes the surface of the sample. In recent years, a method has received attention which specifies various kinds of molecules that constitute biomedical tissue and visualizes a fine two-dimensional distribution state of those molecules, by using SIMS.

In SIMS, secondary ions are emitted by a sputtering phenomenon which occurs by a collision between a primary ion and a molecule in the sample. Conventionally, a monatomic ion of gallium or the like has been used as the primary ion, but when a macromolecule such as a biomaterial has been determined to be a target, in particular, there has been a problem that detection sensitivity is poor, because when the monatomic ion is used, a molecular structure is remarkably decomposed. On the other hand, in recent years, a cluster ion of C60, bismuth, argon or the like is progressively used as the primary ion. The cluster ion contains a large number of atoms and molecules in one ion, and accordingly kinetic energy per one atom and one molecule is small. Accordingly, the decomposition of the molecular structure of the molecule in the sample can be alleviated. Furthermore, a sputtering yield by the cluster ion (number of atoms in sample, which are emitted per one primary ion) is high. Due to these effects, when the cluster ion is used, a yield of the secondary ion (number of secondary ions detected per one primary ion) in SIMS is enhanced, and in particular, the detection sensitivity for the secondary ion having a large mass is improved. However, the generation efficiency of the cluster ion is lower than that of the monatomic ion, and accordingly the number of the ions (corresponding to electric current value of ion) included in one irradiating ion group is generally small. For this reason, the amount of the secondary ions obtained by one time of irradiation with the ion group becomes very small, and in order to obtain a signal having sufficient intensity, it is necessary to enormously repeat the analysis cycle formed of irradiation with the primary ion and measurement of the secondary ion and integrate the data. From the above reasons, when the cluster ion is used in SIMS, there is a problem that a large amount of time periods is needed for the analysis for the sample.

The cluster ion can be obtained by jetting neutral particles of a material into a vacuum, generating neutral cluster particles by adiabatic expansion, and then ionizing the generated neutral cluster particles by an ionizing method such as electron bombardment. Here, the generation efficiency of the cluster ion can be enhanced and the average size of the cluster ion (number of atoms or molecules constituting the cluster ion) can be also increased by increasing a jet pressure to be applied when the material is jetted into the vacuum.

When the material is intermittently jetted with the use of an intermittent valve, the jet pressure per one time of jet can be increased, and accordingly the cluster ion having a large cluster size can be efficiently generated. Japanese Patent No. 3530942 discloses an apparatus which intermittently sprays a liquid material, desolvates the sprayed material to form a neutral cluster molecule, then photoionizes the neutral cluster molecule and thereby efficiently generates the cluster ion of the material.

On the other hand, a technology has been progressively developed which strictly limits the kinetic energy of the atom and the molecule which constitute the cluster ion, reduces the decomposition of the sample as much as possible and thereby secures the yield of the secondary ion. Japanese Patent Application Laid-Open No. 2011-29043 discloses an apparatus which controls the kinetic energy per one atom in the gas cluster ion to 20 eV or less.

There has been a problem in a conventional SIMS apparatus that the detection sensitivity is insufficient. When the cluster ion is used as the primary ion in order to solve this problem, it is necessary to enormously repeat the analysis cycle formed of irradiation with the primary ion and measurement of the secondary ion in order to obtain the mass spectrum and the mass distribution image of the secondary ions having sufficient intensity, and accordingly there has been a problem that a large amount of time periods is needed.

When the intermittent valve described in Japanese Patent No. 3530942 is used, the generation efficiency of the cluster can be improved. However, the operation (opening and closing) time cycle of the above described intermittent valve is as long as 20 msec to 1 sec, while the time cycle of the analysis cycle in a general SIMS apparatus is several hundreds psec, and accordingly when the intermittent valve is combined with SIMS, the operation cycle of the intermittent valve becomes the rate-limiting factor of the time cycle of the analysis cycle. From the above description, even if the efficiency of cluster generation is improved and the repeat count of the cycles can be reduced due to the use of the intermittent valve, the total time period necessary for all the repeat counts cannot be still shortened.

When the apparatus described in Japanese Patent Application Laid-Open No. 2011-29043 is used, the decomposition of a molecule in the sample can be suppressed, and accordingly a high yield of the secondary ion can be secured. However, because the gas is continuously jetted, it is difficult for the jet pressure to be raised, from the viewpoint of keeping a vacuum. As a result, the efficiency of cluster generation is not enhanced, and the amount of the secondary ions which are obtained by one time of irradiation with the ion group is still very small. Accordingly, even if the apparatus in Japanese Patent Application Laid-Open No. 2011-29043 is used, an enormous number of integrations is needed, and accordingly an analysis time period cannot be still shortened.

SUMMARY OF THE INVENTION

The present invention provides an ion group irradiation device that is an ion group irradiation device for irradiating a sample with an ion group, and includes: an ion source that generates an ion; and an ion group selecting unit that selects an ion group including a cluster ion from ions released from the ion source, wherein the ion source has a pressure gradient forming unit for changing a pressure with which a material of the cluster ion is jetted, with time, the ion group selecting unit has a chopper which performs a chopping operation of selecting the ion group by passing and blocking the cluster ions in a traveling direction by the opening and closing of the chopper, and the chopper performs two or more times of the chopping operations per one time of a pressure gradient forming operation by the pressure gradient forming unit. According to the ion group irradiation device of the present invention, detection sensitivity to the secondary ion in one time of irradiation with the ion group can be enhanced, and the analysis cycle including the irradiation with the ion group and the measurement of the secondary ion can be performed in a short time cycle. Thereby, the mass spectrum and the mass distribution image of the secondary ions having sufficient intensity can be obtained in a short time period.

Further features of the present invention will become apparent from the following description of exemplary embodiments with reference to the attached drawings.

BRIEF DESCRIPTION OF THE DRAWINGS

FIG. 7 is a schematic view for illustrating an outline of a configuration of a device according to an eighth embodiment of the present invention.

FIG. 8 is a schematic view for illustrating (a) a timing chart example of an intermittent valve, (b) a timing chart example of a first deflecting electrode and (c) a timing chart example of a second deflecting electrode, according to a twelfth embodiment of the present invention.

DESCRIPTION OF THE EMBODIMENTS

Preferred embodiments of the present invention will now be described in detail in accordance with the accompanying drawings.

Detailed embodiments of the present invention will be described below. Incidentally, the application of the ion irradiation device of the present invention is not limited in particular, and may be used as one part of the secondary ion mass spectrometer, and may also be used as a surface treatment apparatus or a surface modification apparatus. The embodiments will be described in detail below in which the ion irradiation device is used as one part of the secondary ion mass spectrometer. However, the following description in each of the embodiments and the drawings is consistently the illustration of the present invention, and even in the case where the point is not particularly mentioned, the present invention is not limited to those descriptions. In addition, also in the case where the present invention is carried out in combination with a plurality of exemplary embodiments in such a range as not to cause contradiction, the case is included in a range which the present invention targets.

First Embodiment

Figure 1:
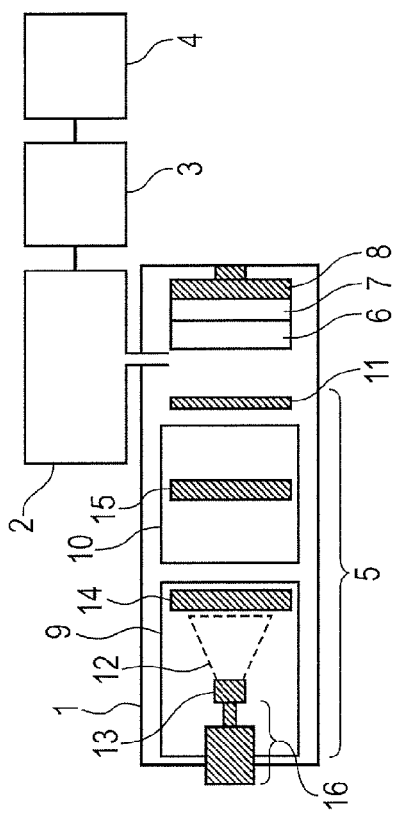
FIG. 1 is a schematic view for illustrating a configuration of a device according to a first embodiment of the present invention.

FIG. 1 is a schematic view for describing a device of the present embodiment. The device of the present embodiment includes a primary ion irradiation device 1 for irradiating a sample with a primary ion, and a mass spectrometer 2 for subjecting the generated secondary ion to mass spectrometry. In addition, the device includes an analysis apparatus 3 for conducting analysis processing for the mass spectrum and the mass distribution image of the obtained secondary ion, and an output apparatus 4 for outputting the mass spectrum and the mass distribution image.

The primary ion irradiation device 1 of FIG. 1 has a primary ion irradiation unit 5, and a sample holding unit 8 which holds a sample 6 on a substrate 7. In addition to these, the device may additionally have a not-shown mass spectrometry unit for obtaining the mass spectrum of the ion group which is the primary ion. The primary ion irradiation unit has an ion source 9, an ion group selecting unit 10 and an ion group irradiation unit 11. An ion group including a cluster ion is selected from ions which have been released from the ion source 9, by the ion group selecting unit 10. The selected ion group is accelerated to several to several tens keV due to a potential difference between the ion group selecting unit 10 or the ion group irradiation unit 11 and the surface of the sample, and irradiates a particular region on the surface of the sample. In the present specification, an irradiating ion group is occasionally referred to as the primary ion. Incidentally, the ion group irradiation unit 11 may be one part of the ion group selecting unit 10, and in the case, the ion group irradiation unit 11 does not need to be additionally provided. In addition, the ion group irradiation unit 11 may include a converging electrode which converges the irradiation diameter of the ion group, a reaccelerating electrode which reaccelerates the ion, a deflecting electrode which deflects the ion, and the like. The number of the primary ion irradiation unit 5 may be one or two or more pieces. The number of the primary ion irradiation unit 5 can be one, from the viewpoint of the size of the device and the operation cost. In addition, the numbers of the ion source 9, the ion group selecting unit 10 and the ion group irradiation unit 11 which are included in the one primary ion irradiation unit 5 may be each one or two or more pieces.

The ion source 9 includes an ion material supply unit 16 for jetting neutral particles or ions (hereinafter referred to as material of ion as well) which become a material of the cluster ion into an jet space 12 that is kept at a vacuum. The ion material supply unit 16 has an opening which jets the material of the ion into the jet space 12, and includes at least a pressure gradient forming unit for changing a pressure with which the material of the ion is jetted from the opening, with time. In addition, the ion material supply unit 16 may include a pipe for transferring the material of the ion therethrough to a direction of the jet space, and an ion material retaining unit such as a reservoir and a cylinder, which retains the material of the ion therein. Alternatively, the ion material retaining unit may be connected from the outside of the ion material supply unit 16 through a valve or a regulator. In addition, the ion material supply unit 16 may include a mechanism for adjusting a temperature and a pressure in order to change a phase of the material of the ion, in addition to the pressure gradient forming unit. The whole of the ion material supply unit 16 may be housed in the ion source and the primary ion irradiation device, and one part, for instance, such as a large-sized gas cylinder, may be arranged in the outside of the primary ion irradiation device.

In the ion material supply unit 16, the space in a side closer to the ion material retaining unit than the pressure gradient forming unit is filled with a material of the ion having a pressure which is higher than that in the jet space and is almost constant. The pressure gradient forming unit performs a pressure gradient forming operation, and thereby a gradient of the pressure of the above described material of the ion is formed in the space in the side closer to the jet space than the pressure gradient forming unit. As a result, the pressure of the material of the ion to be jetted changes with time. The above pressure gradient forming unit can inject the material of the ion with a high pressure while keeping the jet space at the vacuum, and accordingly the efficiency of cluster ion generation can be enhanced.

The opening which jets the material of the ion therethrough may be one part of the pressure gradient forming unit, and may also be one part of a pipe which is different from the pressure gradient forming unit. The shape of the opening is not limited in particular, but the smallest cross section in the opening can be a circular shape having 0.01 to 5 mmφ. In addition, the nozzle shape of the above described opening may be a cylindrical type, a conical type, or also a Laval type. Alternatively, the conical nozzle or the Laval nozzle may be separately connected to the tip in the side of the jet space of the ion material supply unit 16.

The pressure gradient forming unit may be arranged on the boundary between the ion material supply unit 16 and the jet space 12, and may also be arranged in a region which is closer to the ion material retaining unit than the boundary between the ion material supply unit and the jet space. When the pressure gradient forming unit is arranged on the boundary between the ion material supply unit 16 and the jet space 12, the material of the ion is jetted from the opening of the pressure gradient forming unit into the jet space. When the pressure gradient forming unit is arranged in the region which is closer to the ion material retaining unit than the boundary between the ion material supply unit and the jet space, a pipe which transfers the material of the ion is arranged between the pressure gradient forming unit and the jet space. In this case, the material of the ion is supplied into the pipe through the pressure gradient forming unit, is transferred in the pipe, reaches the opening which is the boundary between the pipe and the jet space 12, and is jetted from the opening of the pipe into the jet space. However, in this case, the pressure gradient occasionally results in decreasing, by the time when the material of the ion reaches the opening of the pipe. Accordingly, in order to obtain a large jet pressure while keeping the space at a vacuum, the pressure gradient forming unit can be arranged on the boundary between the ion material supply unit 16 and the jet space 12.

The pressure gradient forming unit may be an intermittent valve for changing a flow rate at which the material of the ion passes, with time, or may also be a heater or a laser which instantly heats the material of the ion. However, the intermittent valve can be used from the viewpoint of the reproducibility of the pressure gradient and a response time period. The intermittent valve means a valve which has the opening and has a function of intermittently repeating an opened state (Open) and a closed state (Close). The intermittent valve may have a function which does not completely intercept the opening even in a closed state. However, the opening can be completely intercepted in the closed state from the viewpoint of keeping the jet space at a vacuum.

In the intermittent valves, there are types of a gate valve, a globe valve, a ball valve, a butterfly valve, a needle valve, a diaphragm valve and the like, according to a structure of the valve element. In the intermittent valves, there are also types of an electromagnetic valve, an electrically-powered valve, an air valve, a hydraulic valve and the like, according to a system of driving the valve element. Any type of valve can be used for the intermittent valve of the present invention. However, the electromagnetic valve can be used from the viewpoint of a response speed. In the electromagnetic valves, there are types of a poppet type, a spool type, a sliding type and the like, according to an opening and closing mechanism of a valve seat, but any type of electromagnetic valve may be used.

The embodiments will be described in detail below in which the intermittent valve is arranged on the boundary between the ion material supply unit 16 and the jet space 12. However, the present invention is not limited to these descriptions.

When the intermittent valve is in the closed state (Close), the material of the ion is separated from the jet space which is kept at the vacuum, on the border of the opening. When the intermittent valve is switched from the closed state (Close) to the opened state (Open), the material of the ion is jetted from the opening into the jet space at supersonic speed. The jetted material of the ion is cooled by adiabatic expansion, and one part of the material of the ion becomes a neutral cluster or a cluster ion. The degree of vacuum in the jet space in a steady state in which the intermittent valve is set at Close is not limited in particular, but can be 1 Pa or less in order to keep the efficiency of cluster generation high. In addition, the jet pressure of the material of the ion in the steady state in which the intermittent valve is set at Close is not limited in particular. The jet pressure of the material of the ion can be high, from the viewpoint of the efficiency of cluster generation. However, when the jet pressure is excessively high, it becomes difficult to keep the jet space at the vacuum when the intermittent valve is set at Open, and accordingly the jet pressure of approximately 0.01 to 10 MPa can be employed. In addition, the jet pressure of the material of the ion can be kept constant during measurement, but when the cluster size or the electric current value of the cluster ion to be generated vary, the jet pressure of the material of the ion may be changed.

The cluster means a substance in which two or more of atoms or molecules are bonded by interaction such as the Van der Waals force, the electrostatic interaction, hydrogen bonding, metal bonding and covalent bonding, and the cluster ion means a cluster which is electrically charged. In addition, the cluster ion may be formed of a single kind of atoms or molecules, and may also be formed of two or more kinds of atoms or molecules. The cluster ion can be formed by generating the neutral cluster by jet with the above described intermittent valve and ionizing the neutral cluster with an ionizing unit 14 which is installed downstream of the jet space.

In the present embodiment, examples of the cluster ion can include: the cluster ion formed of gold, bismuth, xenon, argon and water; and an ion of fullerene which is the cluster formed of carbon.

The cluster ion of gold can include a cluster ion formed of 2 to 1,000 gold atoms which are bonded by the metal bond and are ionized. The cluster ion of bismuth can include a cluster ion formed of 2 to 1,000 bismuth atoms which are bonded by the metal bond and are ionized. The cluster ion of argon can include a cluster ion formed of 2 to 100,000 argon atoms which are agglomerated by the Van der Waals force and are ionized. The cluster ion of water can include a cluster ion formed of 2 to 100,000 water molecules which are bonded by the hydrogen bond and are ionized. The cluster ion of carbon can include a cluster ion formed of fullerene that is formed of 60 carbon atoms which are bonded by the covalent bond or 2 to 1,000 fullerenes that are further agglomerated by the Van der Waals force, and are ionized.

Incidentally, in the present specification, when the ion is the cluster ion, one piece of the cluster ion is regarded as one ion, regardless of the kind of bonding in the cluster; and the mass of the ion means a mass obtained by deducting the mass of a deficient electron from the sum of the mass of the atoms constituting the ion, or a mass obtained by adding the mass of an added electron to the sum. In addition, in the present specification, there is the case where a word of particle is used as a concept including an atom, a molecule and a cluster.

Figure 2:
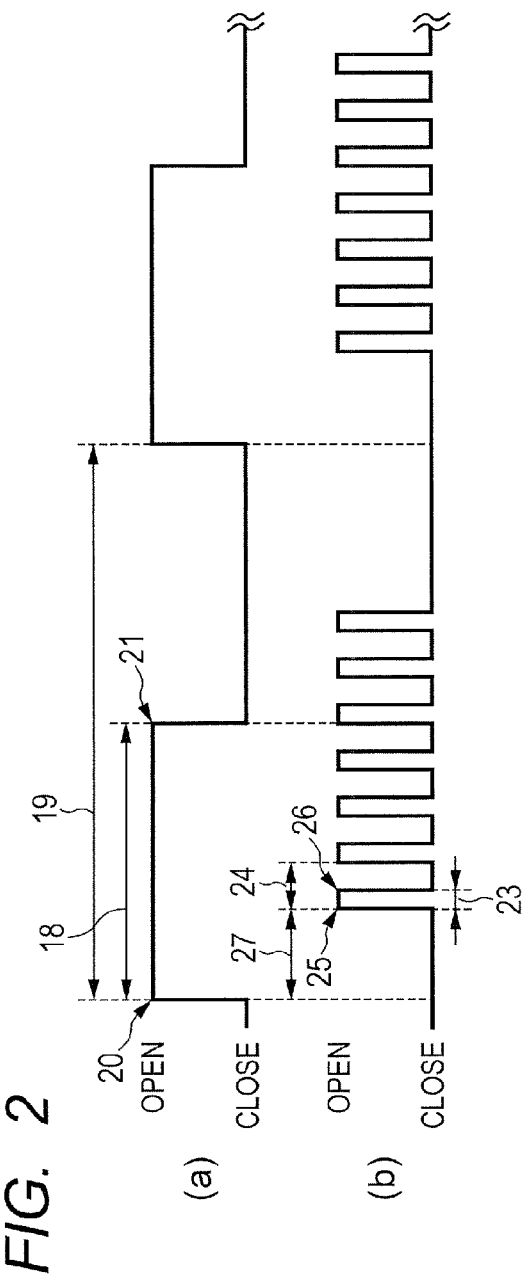
FIG. 2 is a schematic view for illustrating (a) a timing chart example of an intermittent valve, and (b) a timing chart example of a chopper, according to the first embodiment of the present invention.

The cluster ion which has been generated in the ion source 9 is guided to the ion group selecting unit 10, and is subjected to two or more times of chopping operations per one jet by an intermittent valve 13, by a chopper 15 in the ion group selecting unit. (a) and (b) of FIG. 2 illustrate an example of timing charts of an jet operation by the intermittent valve 13 and a chopping operation by the chopper 15. As is illustrated in the timing chart of the intermittent valve in (a) of FIG. 2, a time period while the intermittent valve 13 is opened is referred to as an opened time period 18 of the intermittent valve, a time period between the time after the intermittent valve 13 has been opened and the time before the intermittent valve is next opened is referred to as an opening interval 19 of the intermittent valve, the time when the intermittent valve 13 is opened is referred to as an opening time 20 of the intermittent valve, and the time when the intermittent valve 13 is closed is referred to as a closing time 21 of the intermittent valve. The operation of opening and closing the intermittent valve 13 is also referred to as the jet operation. In addition, as is illustrated in the timing chart of the chopper 15 in (b) of FIG. 2, a time period while the chopper 15 is opened is referred to as an opened time period 23 of the chopper, a time period between the time after the chopper 15 has been opened and the time before the chopper is next opened is referred to as an opening interval 24 of the chopper, the time when the chopper 15 is opened is referred to as an opening time 25 of the chopper, and the time when the chopper 15 is closed is referred to as a closing time 26 of the chopper. The opened time period 23 of the chopper corresponds to a time period width of the ion group which is obtained by the opening and closing of the chopper 15. The operation of opening and closing the chopper 15 is also referred to as the chopping operation.

The opened time period 18 and the opening interval 19 of the intermittent valve are as comparatively long as the order of ms at the short, and are longer than the opened time period 23 and the opening interval 24 of the chopper by several digits. The number of the chopping operation by the chopper in the present invention includes two or more times per one jet operation of the intermittent valve. The intermittent valve and the chopper in the present embodiment enable an analysis cycle formed of irradiation with the primary ion having a short time cycle and the measurement of the secondary ion to be performed in a short time cycle, without depending on the opened time period and the opening interval of the intermittent valve. In addition, in the present embodiment, the efficiency of cluster generation is high because the intermittent valve is used, and accordingly the detection sensitivity to the secondary ion per one irradiation with the primary ion is high. As a result, the number of integrations necessary for obtaining a mass spectrum of the secondary ions having sufficient intensity can be reduced. Therefore, according to the present embodiment, the mass spectrum and the mass distribution image of the secondary ions having sufficient intensity can be obtained in a short time period.

Incidentally, the mass spectrum and the mass distribution image of the secondary ions having sufficient intensity, which are obtained in the present embodiment, are not limited in particular, and may have such a degree of intensity that the distributions of the peak and the ion which have received attention can be discriminated, in the mass spectrum and the mass distribution image of the secondary ions, which are in a state of raw data or have been subjected to analysis processing. The mass spectrum of the secondary ions having the sufficient intensity can have a signal/noise ratio of the peak which has received attention of 3 or more in the raw data, and the mass distribution image having the sufficient intensity can be an image which is reconstructed with the use of the peak.

The opened time period 18 of the intermittent valve is not limited in particular, but the time period generally within a range of 1 to 50 msec is used. The opening interval 19 of the intermittent valve is not limited in particular as long as the opening interval 19 is larger than the opened time period 18 of the intermittent valve, but the time period generally within a range of 1 to 100 msec is used. In addition, the opening interval 19 and the opened time period 18 of the intermittent valve may be constant and may also change. Incidentally, the opened time period 18 and the opening interval 19 of the intermittent valve can be constant, while the analysis cycle formed of irradiation with the primary ion and the measurement of the secondary ion is repeated on the same region of the same sample, from the viewpoint of repetition stability. However, there is the case where the size of the cluster included in the ion group and the electric current value vary with the passage of the time period, and the intensity of the secondary ion varies in every cycle. In this case, the above described opened time period 18 and opening interval 19 of the intermittent valve can be changed, based on the fluctuation of the intensity of the secondary ion, and on the fluctuation of the ion group to be evaluated with the use of a mass spectrometry unit for the primary ion and a unit for measuring an electric current value of the primary ion, which are separately installed in the primary ion irradiation device.

The opened time period 23 of the chopper is not limited in particular, but the time period generally within a range of 0.5 nsec to 50 μsec is used. The opening interval 24 of the chopper is not limited in particular as long as the opening interval 24 is shorter than the opening interval 19 of the intermittent valve, but can be longer than a time period during which a sample is irradiated with the ion group generated by the chopper and the generated secondary ion is measured with a mass spectrometer. Because of this, the opening interval generally within a range of 10 μsec to 1 msec is used. In addition, a difference 27 of the opening time between the opening time 20 of the intermittent valve and the opening time 25 of the chopper is not limited in particular, and the opening times may be the same time. When one jet operation of the intermittent valve is determined to be one cycle, the above described difference 27 of the opening time may be constant or may also change in every cycle. Incidentally, the above described difference 27 of the opening time can be constant, while the analysis cycle formed of irradiation with the primary ion and the measurement of the secondary ion is repeated on the same region of the same sample, from the viewpoint of repetition stability. However, there is the case where the size of the cluster included in the ion group and the electric current value vary with the passage of the time period, and the intensity of the secondary ion varies in every cycle. In this case, any of the above described opened time period 18 and opening interval 19 of the intermittent valve, the opened time period 23 and opening interval 24 of the chopper, and the difference 27 of the opening time between the opening time 20 of the intermittent valve and the opening time 25 of the chopper can be changed, based on the fluctuation of the intensity of the secondary ion, and on the fluctuation of the ion group to be evaluated with the use of the mass spectrometry unit for the primary ion and the unit for measuring the electric current value of the primary ion, which are separately installed in the primary ion irradiation device.

A method for driving the opening and closing operation of the intermittent valve is not limited in particular, and an appropriate driving method may be selected according to the type of intermittent valve. When the intermittent valve is the electromagnetic valve, the opening and closing operation of the intermittent valve can be accurately performed by supplying voltage while using a waveform generator. In addition, it is also possible to branch a voltage application signal sent to the intermittent valve, and to send the above described branched signals to the chopper as a trigger signal, at the same time or at the delayed time by a fixed time period through a delay time generating apparatus. In this case, the jet operation of the material of the ion by the intermittent valve can be accurately interlocked with the chopping operation by the chopper.

When one jet operation of the intermittent valve is set at one cycle, the number of the cycles is not limited in particular as long as the number is one or more times. In addition, the number of the chopping operations of the chopper in the above described one cycle is not limited in particular as long as the number is two or more times. The number of the chopping operations can be set, for instance, at 5 times or more, 10 times or more, 50 times or more, 100 times or more, 200 times or more, 500 times or more, 1,000 times or more, 10,000 times or more or the like. However, if the above described number of the cycles and number of the chopping operations are set at the minimum number in a range of being capable of acquiring the mass spectrum and the mass distribution image of the secondary ions having sufficient intensity, the analysis time period can be shortened.

The shape of the opening of the intermittent valve 13 is not limited in particular, but the smallest cross section in the opening can be a circle having 0.01 to 5 mm$\phi$. In addition, the conical nozzle or the Laval nozzle may be connected to the above described opening. Alternatively, the intermittent valve may have the conical nozzle or the Laval nozzle incorporated in the opening.

The material of the ion means a substance that becomes a material of the ion which will irradiate a sample as a primary ion. The material of the ion is an aggregate of the neutral or charged particles, and the kind and the state are not limited in particular. The kind of atom or molecule which constitutes the above described particles may be a single substance or a plurality of substances forming a mixture. The state of the material of the ion at normal temperatures and normal pressures may be any one of gas, liquid and solid; may also be a mixed state of gas and liquid; and may also be a state in which solid is dissolved in gas or liquid. However, when the state is solid, the phase of the material of the ion needs to be converted to liquid or gas which can be jetted by the intermittent valve, in the ion material supply unit 16. Examples of the above described gas can include a noble gas such as argon and xenon, and oxygen. Examples of the above described liquid can include water, acid, alcohol and alkali. Examples of the above described solid can include metal such as gold and bismuth, and fullerene.

The ionic species included in the ion group which irradiates the sample may be appropriately selected according to the kind of molecule in the sample that is an object to be detected. For instance, there is the case where the detection sensitivity can be enhanced by the intentional addition of an ion to a target molecule. Examples of the ion to be added include a hydrogen ion, a sodium ion, a potassium ion, an ammonium ion, a silver ion, a gold ion and a chlorine ion.

The ionic species included in the ion group which irradiates the sample can be selected by the selection of the material of the ion to be used and the ion group selecting unit. When the addition of the hydrogen ion is intended, for instance, any one of water, an acid and an alcohol is added into the material of the ion, and thereby the ionic species which abundantly contain hydrogen can be easily produced. In addition, when the addition of the sodium ion, the potassium ion, the ammonium ion, the silver ion, the gold ion or the chlorine ion is intended, an organic salt or an inorganic salt containing sodium, potassium, silver, gold or chlorine may be added into the material of the ion. Representative substances of the sodium salt include sodium formate, sodium acetate, sodium trifluoroacetate, sodium hydrogen carbonate, sodium chloride and sodium iodide. Even though the organic salt or the inorganic salt itself is a solid, the salt can be easily used as the material of the ion by the addition of the salt, for instance, to a liquid such as water.

Furthermore, the ion source 9 has an ionization unit 14, when the material of the ion is a neutral particle which is not electrically charged, in other words, is a neutral atom or molecule, or is a neutral cluster. The ion source 9 may also have a mechanism which heats and pressurizes the material of the ion, a skimmer which removes large neutral particles, and a buffer container for differential evacuation, as needed. In addition, the ion source 9 may have a function of classifying ions into ion groups according to every mass to generate the ion groups. The ion source 9 may have, for instance, a temperature controller which separates the ions by a difference of the boiling point or the melting point, an aerodynamic particle-size distribution measuring apparatus which separates the ions by a difference of the particle size.

An ionizing method with the ionization unit 14 is not limited in particular, and can include an electron bombardment ionization method, a chemical ionization method, a photoionization method, a surface ionization ionizing method, a field emission method, a plasma ionization method, a Penning ionization method and an electrospray method. In order to ionize gases of the noble gas such as argon and xenon, and oxygen, for instance, the electron bombardment ionization method is employed for the neutral cluster particles that are generated by the jet of the noble gas into a vacuum from a nozzle, and thereby a monatomic ion and a cluster ion can be obtained. In addition, in order to ionize a liquid such as water, an acid, an alcohol and an alkali, the liquid is heated into gas by the ion material supply unit 16, the gas is ionized by the electron bombardment ionization method in a similar way to the above described noble gas, and thereby the monomolecular ion and the cluster ion can be obtained. As for another method, water, an acid or an alcohol in the state of liquid is passed through a nozzle in the vacuum, and a high voltage of approximately several kV is applied to the tip of the nozzle. Thereby, the liquid can be ionized by the electrospray method. In addition, in order to ionize metal such as gold and bismuth, the metal coated on a tungsten emitter is heated in the vacuum, and an electrostatic field is applied between a drawing electrode and the tip of the emitter. Thereby, the monatomic ion and the cluster ion can be obtained by the field emission method. In order to ionize fullerene, the fullerene is heated into gas by the ion material supply unit 16, the gas is ionized by the electron bombardment ionization method in a similar way to the above described noble gas, and thereby the monomolecular ion and the cluster ion can be obtained. Incidentally, the ionization unit may continuously perform ionization, or may also intermittently perform ionization.

The ion group selecting unit 10 contains at least one or more choppers 15. The chopper 15 is a unit of intermittently passing the ions by repeating an opened state (Open) and a closed state (Close). The ions are divided into parts in a traveling direction by the chopper 15, and one or more pieces of ion groups are selected. The chopping operation means an operation of selecting one or more pieces of ion groups by passing and blocking the ions in a traveling direction by the opening and closing of the chopper. The chopper intercepts the ions in the traveling direction in the closed state, and passes the ions in the traveling direction in an opened state. Such an operation of the chopper as to start from the closed state, pass through the opened state in a fixed time period and reach the opened state again, is counted as one chopping operation. The structure of the chopper 15 is not limited in particular, and the structure that can be used includes: a combination of a deflecting electrode with an opening; a mesh-shaped retarding electrode; and a circular flat plate provided with an opening, which rotates at high speed. An ion group having a short time period width can be obtained by the chopping operation by the chopper 15. The ion group having the short time period width can be obtained by the chopper 15, thereby the time period width between the ion groups when the ion groups reach the sample can be shortened, and accordingly a mass resolution for the secondary ion can be enhanced.

A method for driving the opening and closing operations of the chopper 15 is not limited in particular, and an appropriate driving method may be selected according to the type of chopper. When the chopper is formed of the combination of the deflecting electrode with the opening, voltage is supplied to the deflecting electrode with the use of a waveform generator, and thereby the opening and closing operations of the chopper can be accurately performed. In addition, it is also possible to branch a voltage application signal sent to the deflecting electrode, and to send the above described branched signals to a mass spectrometer as a trigger signal, at the same time or at the delayed time by a fixed time period through a delay time generating apparatus. In this case, the chopping operation by the chopper can be accurately interlocked with the measurement of the secondary ion by the mass spectrometer.

The ion group selecting unit 10 may include various ion separators, in addition to the chopper. The ion separator means a unit of separating an aggregate of ions formed of a plural kinds of ions, in a gas phase, according to each property (mass, number of electric charge, three-dimensional shape and the like) of the ions. The ion separator is not limited in particular, and the ion separator which can be used includes a time-of-flight mass separator, a quadrupole type mass separator, an ion trap type mass separator, a magnetic field type mass separator, an ExB filter and an ion mobility meter.

When the ion groups irradiate the sample, the ion groups may be converged and irradiate the sample as a scanning type which scans the sample, or may irradiate the sample as a projection type which collectively irradiates a specific region of the sample.

In the case of the scanning type, the irradiating ion group is converged with the use of a converging electrode, is further deflected with the use of a deflecting electrode, thereby irradiates a microscopic region on the sample, and scans the sample. An irradiation diameter is not limited in particular, but can be approximately 0.01 to 50 µmϕ because the irradiation diameter directly affects a spatial resolution of the mass image which is obtained by a secondary ion mass spectrometry.

In the case of the projection type, the irradiation diameter for irradiation of the ion groups is converged or expanded with the use of the converging electrode, and the ion groups are deflected with the use of the deflecting electrode, as needed. Thereby, the ion groups irradiate collectively the specific region of the sample. The irradiation diameter in the projection type is not limited, but can be approximately 0.01 to 10 mmϕ because the irradiation diameter corresponds to the area of a region to be measured.

The average mass of the ions which constitute the ion group is not limited in particular. As the mass of the primary ion is larger, the fragmentation of the molecule in the sample is more suppressed. Accordingly, the yield of the secondary ion is enhanced. On the other hand, when the mass is excessively large, there is the case where the number of the ions contained in the ion group decreases. The average mass of the ion groups as the primary ion can be appropriately selected, according to the molecular weight and the kind of molecule which constitutes the region that is the target.

The sample 6 is a solid or a liquid, and includes an organic compound sample, an inorganic compound sample and a biological sample. Examples of a method of fixing the sample include a method of fixing the sample on a flat substrate 7 and holding the flat substrate on a sample holding unit 8.

The material of the substrate 7 is not limited, but metal such as gold, ITO, and silicon or glass coated with the metal or the ITO can be used from the viewpoint of suppressing the electric charging of the sample 6, which is caused by irradiation with the primary ion and the emission of the secondary ion.

The sample holding unit 8 has a region for holding the sample 6 and the substrate 7 thereon, and may further have an electric current value measuring unit such as a Faraday cup for measuring the electric current value of the ion groups which irradiate the sample 6. The sample holding unit 8 may also be provided with a temperature control mechanism which heats or cools the sample.

The sample holding unit 8 can be moved and rotated in a horizontal direction, or can be moved in a height direction. The region and height for irradiation with the primary ion can be adjusted by control in an in-plane direction and a height direction. Furthermore, a sample holding mechanism can also be desirably inclined. The incident angle of the primary ion with respect to the surface of the sample can be controlled by the control of the inclination.

The ion irradiation device according to the present invention can generate at least two or more pieces of ion groups including the cluster ion, with sufficient throughput. The two or more pieces of the ion groups may irradiate the same surface region of the same sample, and may irradiate a plurality of different surface regions of the same sample. The two methods may be used so as to suit each of the samples and the regions.

When the two or more pieces of the ion groups irradiate the same surface region of the same sample, the secondary ion mass spectrometry of the region to be irradiated with the ion groups can be performed with sufficient throughput. In addition, when the surface treatment or the surface modification is the purpose, the cluster ion can irradiate the sample at a high-speed cycle. Because of this, the surface which has been subjected, for instance, to etching, flattening and coating treatment can be obtained in a short time period.

When a plurality of different surface regions of the same sample is irradiated with the ion groups, the plurality of surface regions and the large area can be subjected to the secondary ion mass spectrometry with sufficient throughput. In addition, previous examination for selecting the ion group which is suitable for the target molecule can be performed on each of the surface regions with sufficient throughput. In addition, when the surface treatment or the surface modification is the purpose, the cluster ion can irradiate the plurality of surface regions at a high-speed cycle. Because of this, the surface which has been subjected to different treatments, for instance, of etching, flattening and coating on respective regions, or the surface having a wide area which has been subjected to the treatment can be obtained in a short time period.

The number of times of irradiation with the ion groups (number of irradiating ion groups) is not limited in particular. When the same region of the same sample is irradiated with the ion groups more than once, the operation can also be ended before the amount of the irradiating ions reaches a static limit or more. The static limit is such a level that the probability of the occurrence that another ion collides against a point again against which an ion has collided once is neglectable. The amount of irradiation with the ions at this time is 1% or less of the atoms or the molecules which constitute the surface.

The secondary ion that is generated from the surface of the sample, which is irradiated with the ion group, is measured by the mass spectrometer. The mass spectrometer is provided with an extraction electrode which extracts the secondary ion in the vicinity of the sample, a mass separating portion which separates the secondary ion that has been extracted by the extraction electrode, according to each of the mass-to-charge ratios, and a detector which detects each of the separated secondary ions.

Furthermore, the mass spectrometer may include a secondary ion group selecting mechanism which selects only one part out of the generated secondary ions as a secondary ion group, in addition to the mass separating portion. By selecting only one part out of the generated secondary ions as the secondary ion group, the secondary ion group selecting mechanism can shorten the time period width of the secondary ions, and accordingly can enhance the mass resolution in a mass spectrum of the secondary ions to be obtained. Incidentally, the secondary ion group selecting mechanism may have a function of selectively selecting the secondary ions based on the mass.

The secondary ion group selecting mechanism may be provided in the extraction electrode, or may also be provided in another component. When being provided in the extraction electrode, the secondary ion group selecting mechanism can select the secondary ion groups, for instance, by shortening the time period width of the voltage application. When another component is used, an electrode for selecting the secondary ion groups is installed between the extraction electrode and the mass separating portion, and the secondary ion groups may be selected by the control of the voltage application to the electrode for selecting the secondary ion groups. In the orthogonal time-of-flight mass spectrometer, for instance, the electrode for selecting the secondary ion groups is installed between the extraction electrode and the mass separating portion, and the mass separating portion is installed in a vertical direction to a traveling direction of the secondary ions which move from the extraction electrode toward the electrode for selecting the secondary ion groups. In this case, the extraction electrode always extracts the secondary ion, repeats ON/OFF of the voltage application to the electrode for selecting the secondary ion groups, thereby selects one part out of the extracted secondary ions as the secondary ion group, and simultaneously can guide the secondary ion groups to the mass separating portion.

A mass separation method in the mass spectrometer 2 is not limited in particular, and various methods such as a flight time type, a magnetic deflection type, a quadrupole type, an ion trap type, a Fourier transform ion cyclotron resonance type, an electric field type Fouler transform type, and a multiturn type can be adopted solely or in combination with other above one or more types.

When the ion groups irradiate the sample as the projection type, a mass spectrometer provided with a detector having a function of two-dimensionally detecting ions is used, and thereby the mass information and the detected positional information on the secondary ion can be simultaneously recorded.

When the ion groups irradiate the sample as the scanning type, the positional information is recorded when the ion groups have irradiated the sample. In this case, only the mass-to-charge ratio of the secondary ion may be measured, and accordingly the detector may be used which is suitable for each mass spectrometric method.

The mass spectrometry result is subjected to analysis processing by the analysis apparatus 3, and can be output by the output apparatus 4 as the mass spectrum of the secondary ions and the mass distribution image which have been subjected to the analysis processing. The analysis processing may include: a calibration of the mass-to-charge ratio; and the integration, averaging and standardization of the mass spectrum which have been obtained by irradiation with the same kind of ion groups. The above described analysis apparatus 3 and output apparatus 4 may be each an integrated circuit provided with a dedicated calculation function and memory, or may be each an apparatus which is constructed in a general-purpose computer as a software.

Second Embodiment

In the present embodiment, a timing of the chopping operation (opening time or closing time) by a chopper or the time which has been delayed by a fixed time period after this timing is used as the measurement start time of a secondary ion by the above described mass spectrometer.

The mass spectrometer is interlocked with the chopper while using the above described start time, which enables the time period between the time when the ion group which has been selected by the chopper irradiates the sample and the time when the secondary ion is measured to be kept constant, even when there are variations in the opening intervals of the intermittent valve and/or the chopper. As a result, it becomes easy to control the apparatuses so as to acquire the mass spectrum or the mass distribution image of the secondary ions with sufficient repeatability.

A time difference between the start time (opening time of chopper) of the chopping operation by the chopper and the measurement start time of the secondary ion with the mass spectrometer is not limited in particular, as long as the time difference is constant while the analysis cycle formed of the irradiation with the primary ion and the measurement of the secondary ion is repeated on the same region of the same sample. For instance, a time period which the ion group that has been selected by the chopper spends before reaching the sample due to the ion group irradiation unit can be used as the above described time difference.

Other parts of the constitution are similar to those in Embodiment 1.

Third Embodiment

The present embodiment includes that the operation time period of the operation of measuring the secondary ion by the above described mass spectrometer is shorter than the opening interval of the chopping operation by the above described chopper.

In the present embodiment, the measurement time period of the secondary ion by the mass spectrometer is not limited in particular. However, if the measurement time period by the mass spectrometer is controlled so as to be shorter than the opening interval of the chopping operation by the chopper, the measurement of the secondary ion can be performed once per one selecting of the ion group and irradiation with the ion group. As a result, the analysis cycle formed from the irradiation with the ion group and the measurement of the secondary ion can be performed in a shorter time cycle. For this reason, the measurement time period by the mass spectrometer can be shorter than the opening interval of the chopping operation by the chopper.

Figure 3:
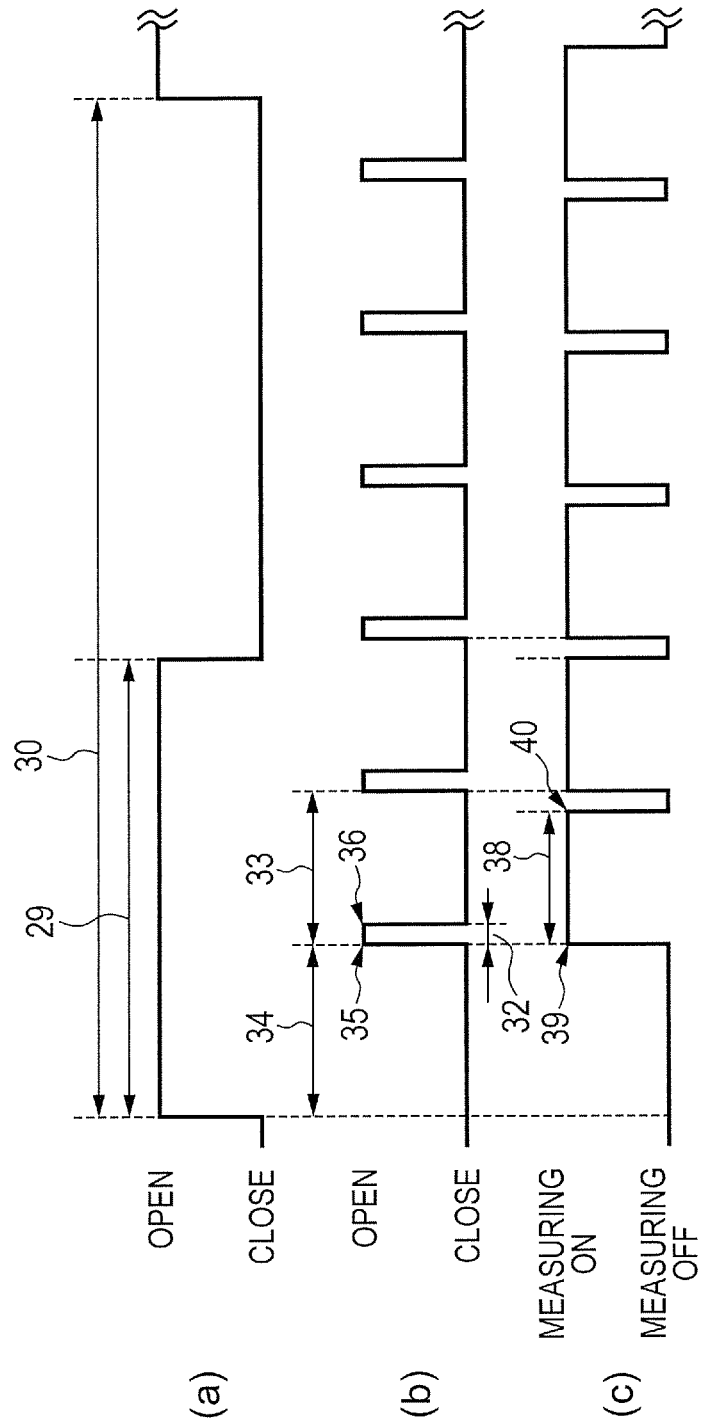
FIG. 3 is a schematic view for illustrating (a) a timing chart example of an intermittent valve, (b) a timing chart example of a chopper and (c) a timing chart example of a mass spectrometer, according to a third embodiment of the present invention.

In (a) to (c) of FIG. 3 which illustrate timing charts of an intermittent valve, a chopper and a mass spectrometer, respectively, an opened time period 29 and an opening interval 30 of the intermittent valve, an opened time period 32 and an opening interval 33 of the chopper, and a difference 34 between the opening times of the chopper and the intermittent valve are similar to those in the first embodiment. A measurement time period 38 of the secondary ion by the mass spectrometer means a time difference between a measurement start time 39 at which the measurement is turned ON from OFF and a measurement finishing time 40 at which the measurement is turned OFF from ON. In the present embodiment, the measurement time period 38 of the secondary ion by the mass spectrometer is shorter than the opening interval 33 of the chopper. Incidentally, the measurement time period 38 of the secondary ion by the mass spectrometer may be constant or may vary.

In examples illustrated in (b) and (c) of FIG. 3, the measurement start time 39 of the secondary ion by the mass spectrometer is the same time as an opening time 35 of the chopper, but may not be particularly the same time, as long as the measurement time period 38 of the secondary ion by the mass spectrometer is shorter than the opening interval 33 of the chopper. However, the measurement start time 39 of the secondary ion by the mass spectrometer can be the same time as the opening time 35 or a closing time 36 of the chopper, from the viewpoint of controllability. In addition, there is the case where it is prevented that a secondary ion to be measured by certain one time of the operation of measuring the secondary ion becomes contaminated with the secondary ion generated by the previous irradiation with the ion group, by controlling the measurement start time 39 of the secondary ion by the mass spectrometer so as to be later than the opening time 35 of the chopper, and consequently the accuracy of the analysis is enhanced.

A measurement finishing time 40 of the secondary ion by the mass spectrometer is not limited in particular, as long as the measurement time period 38 of the secondary ion by the mass spectrometer is shorter than the opening interval 33 of the chopper. When the measurement start time 39 of the secondary ion by the mass spectrometer is the same time as the closing time 36 of the chopper, for instance, the controllability of the measurement finishing time 40 of the secondary ion becomes adequate by using the start time of the chopper in the next chopping operation. In addition, there is the case where it is prevented that a secondary ion to be measured by certain one time of the operation of measuring the secondary ion becomes contaminated with the secondary ion generated by the next irradiation with the ion group, by controlling the measurement finishing time 40 of the secondary ion by the mass spectrometer so as to be earlier than the opening time of the next chopping operation, and consequently the accuracy of the analysis is enhanced.

Other parts of the constitution are similar to those in Embodiment 1.

Fourth Embodiment

Figure 4:
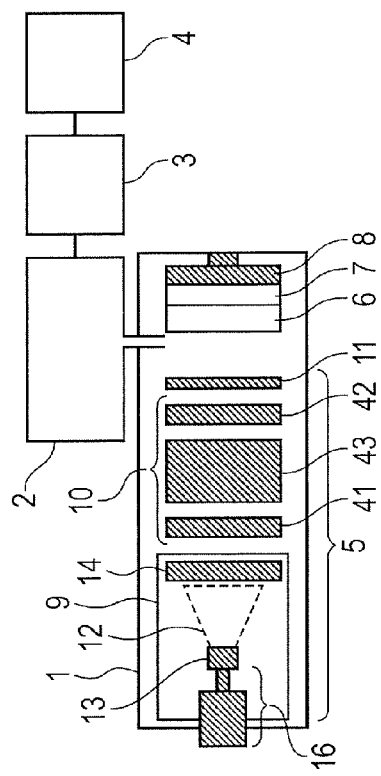
FIG. 4 is a schematic view for illustrating a configuration of a device according to the fourth embodiment of the present invention.

In the device of the present embodiment, as is illustrated in FIG. 4, the ion group selecting unit 10 has a first chopper 41 which is positioned on an ion source side, a second chopper 42 which is positioned in a downstream side of the first chopper 41, and an ion separator 43 which is arranged between the first chopper and second chopper. Furthermore, in the present embodiment, as is illustrated in (b) of FIG. 5, the chopping operation by the first chopper is performed two or more times per one jet operation by the intermittent valve.

The ions released from the ion source 9 contain ions having various masses, and form an aggregate of ions having a wide time period width. The above described time period width of the aggregate of the ions means a width of the time period during which the ions are released from the ion source, and is associated with the opened time period of the intermittent valve. The above described aggregate of the ions firstly reaches the first chopper 41, and is selected as a first ion group containing ions which have a small time period width and various masses, by the chopping operation by the first chopper 41. Next, the first ion group is further separated into each kind of ions by the ion separator 43, and then a chopping operation by the second chopper 42 is performed. By the above operations, a second ion group which has a short time period width and is formed of target ions having a desired mass can be obtained as the second ion group. The ion group irradiation unit irradiates the sample with the second ion group. As the time period width of the irradiating ion group is shorter and the mass of the contained ion is closer to uniformness, the time period width of the ion group, which the ion group spends before reaching the surface of the sample can be less extended, and accordingly the mass resolution of the secondary ion to be generated can be enhanced. Because of this, the first chopper, the second chopper, and the ion separator which is arranged between the first and the second choppers can be suitably used.

Figure 5:
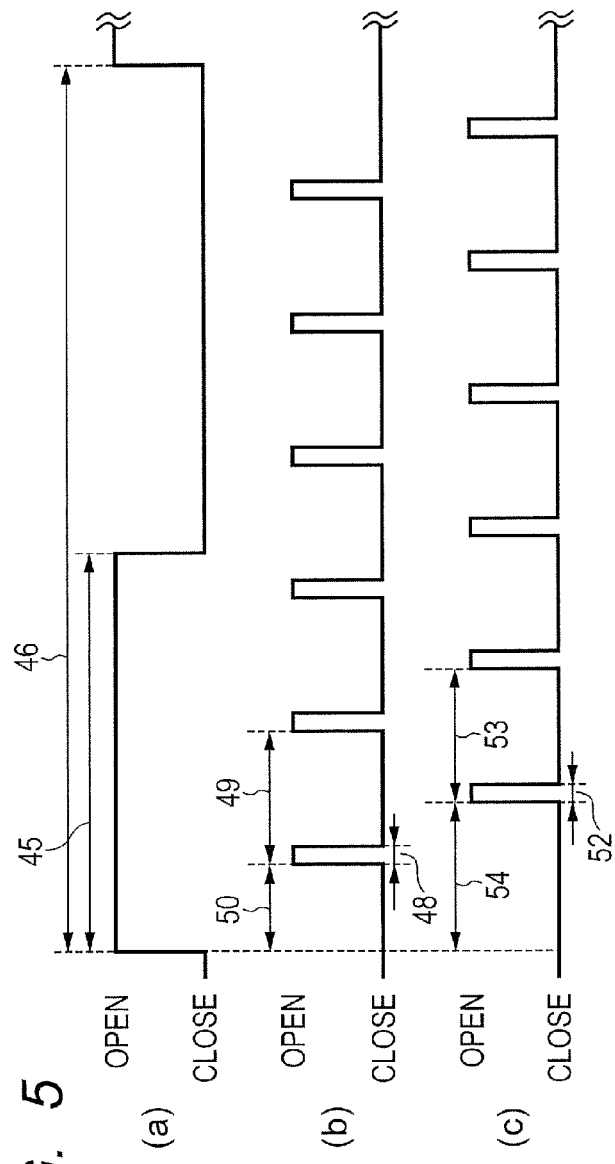
FIG. 5 is a schematic view for illustrating (a) the timing chart example of the intermittent valve, (b) a timing chart example of a first chopper and (c) a timing chart example of a second chopper, according to the fourth embodiment of the present invention.

(a) to (c) of FIG. 5 illustrate timing charts of the intermittent valve, the first chopper and the second chopper in the present embodiment, respectively. An opened time period 45 and an opening interval 46 of the intermittent valve are similar to the description of the intermittent valve in the first embodiment. In addition, an opened time period 48 and an opening interval 49 of the first chopper, and a difference 50 between the opening times of the first chopper and the intermittent valve are similar to the description of the chopper in the first embodiment. An opened time period 52 of the second chopper is similar to the description of the chopper in the first embodiment. An opening interval 53 of the second chopper is not limited in particular, as long as the opening interval 53 is shorter than the opening interval 46 of the intermittent valve, but can be the same as the opening interval 49 of the first chopper, and can be longer than a time period during which the ion group generated by the second chopper irradiates the sample and the generated secondary ion is measured by a mass spectrometer. For this reason, approximately 10 psec to 1 msec are used. In addition, the difference 54 between opening times of the second chopper and the intermittent valve is not limited in particular, as long as the difference 54 is equal to or larger than the difference 50 between opening times of the first chopper and the intermittent valve. However, the difference 54 between the opening times of the second chopper and the intermittent valve can be controlled to be longer than the difference 50 between the opening times of the first chopper and the intermittent valve, by the time period during which the ion group that has been generated by the first chopper is separated by the ion separator and the target ion reaches the second chopper. Incidentally, the opening interval 53 of the second chopper can be constant while the analysis cycle formed of the irradiation with the primary ion and the measurement of the secondary ion is repeated on the same region of the same sample, from the viewpoint of repetition stability, as is illustrated in (c) of FIG. 5. However, there is the case where the size of the cluster included in the ion group and the electric current value vary with the passage of the time period, and the intensity of the secondary ion varies in every cycle. In this case, any one of the above described opened time period 45 and the opening interval 46 of the intermittent valve, the opened time period 48 and the opening interval 49 of the first chopper, the opened time period 52 and the opening interval 53 of the second chopper, the difference 50 of the opening time between the opening time of the intermittent valve and the opening time of the first chopper, and the difference 54 of the opening time between the opening time of the intermittent valve and the opening time of the second chopper can be changed, based on the variation of the intensity of the secondary ion, and the variation of the ion group, which is evaluated with the use of a mass spectrometry unit and/or an electric current value measuring unit for a primary ion, which are installed separately in the primary ion irradiation device.

Other parts of the constitution are similar to those in Embodiment 1.

Fifth Embodiment

In the present embodiment, the same time as a timing of the chopping operation (opening time or closing time) by a first chopper or the time which has been delayed by a fixed time period after the timing is used as the opening time of the chopping operation by a second chopper.

The second chopper is interlocked with the first chopper while using the above described time, which facilitates the control for selecting the ion group having a desired average mass with sufficient repeatability, even when there are variations in the opening intervals of the intermittent valve and/or the first chopper.

A time difference between a start time of the chopping operation (opening time of first chopper) by the first chopper and a start time of the chopping operation (opening time of second chopper) by the second chopper is not limited in particular, as long as the time difference is constant while the analysis cycle formed of the irradiation with the primary ion and the measurement of the secondary ion is repeated on the same region of the same sample. For instance, a time period during which the first ion group that has been selected by the first chopper is separated by the ion separator and an ion having a desired average mass reaches the second chopper can be used as the above described time difference.

Other parts of the constitution are similar to those in Embodiment 4.

Sixth Embodiment

In the present embodiment, the same time as a timing of the chopping operation (opening time or closing time) by a second chopper or the time which has been delayed by a fixed time period after the timing is used as the measurement start time of the secondary ion by the mass spectrometer.

The mass spectrometer is interlocked with the second chopper while using the above described time, which facilitates the control for acquiring the mass spectrum or mass distribution image of the secondary ion having a desired mass range with sufficient repeatability, even when there are variations in the opening intervals of the intermittent valve, the first chopper and the second chopper.

A time difference between the start time of the chopping operation (opening time of first chopper) by the second chopper and the measurement start time of the secondary ion by the mass spectrometer is not limited in particular, as long as the time difference is constant while the analysis cycle formed of the irradiation with the primary ion and the measurement of the secondary ion is repeated on the same region of the same sample. For instance, a time period which the second ion group that has been selected by the second chopper spends before reaching the sample due to the ion group irradiation unit can be used as the above described time difference.

Other parts of the constitution are similar to those in Embodiment 4.

Seventh Embodiment

The present embodiment includes that the measurement time period of the secondary ion by the above described mass spectrometer is shorter than the opening interval of the chopping operation by the above described second chopper.

In the present embodiment, the measurement time period of the secondary ion by the mass spectrometer is not limited in particular. However, if the measurement time period by the mass spectrometer is controlled so as to be shorter than the opening interval of the chopping operation by the second chopper, the measurement of the secondary ion can be performed once per one selecting of the ion group and irradiation with the ion group by the second chopper. As a result, the analysis cycle formed from the irradiation with the ion group and the measurement of the secondary ion can be performed in a shorter time cycle. For this reason, the measurement time period by the mass spectrometer can be shorter than the opening interval of the chopping operation by the second chopper.

Figure 6:
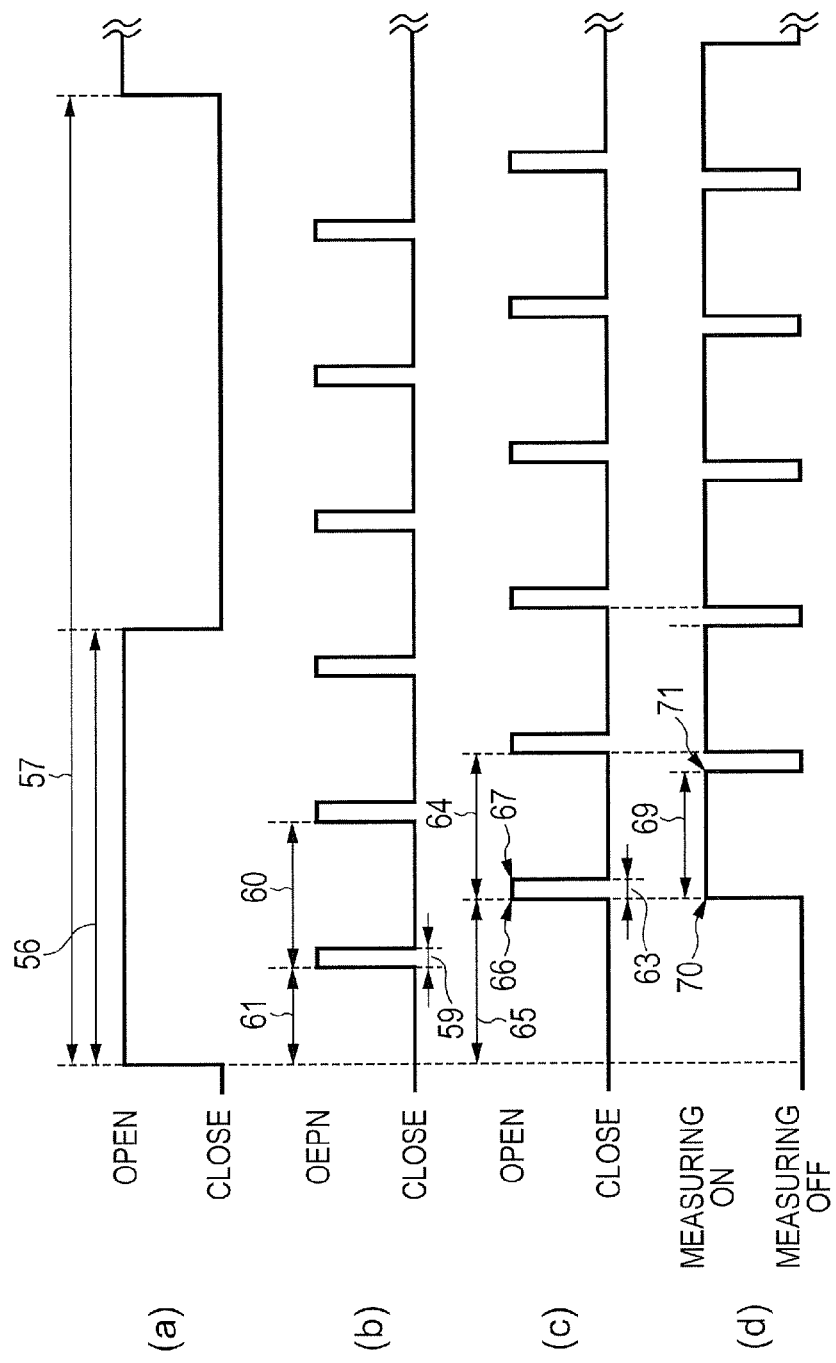
FIG. 6 is a schematic view for illustrating (a) a timing chart example of an intermittent valve, (b) a timing chart example of a first chopper, (c) a timing chart example of a second chopper and (d) a timing chart example of a mass spectrometer, according to a seventh embodiment of the present invention.

In (a) to (d) of FIG. 6 which illustrate a timing chart example of an intermittent valve, a timing chart example of a first chopper, a timing chart example of a second chopper and a timing chart example of a mass spectrometer, respectively, an opened time period 56 and an opening interval 57 of the intermittent valve are similar to the description of the intermittent valve in the first embodiment. An opened time period 59 and an opening interval 60 of the first chopper, and a difference 61 between the opening times of the first chopper and the intermittent valve are similar to the description of the first chopper in the fourth embodiment. An opened time period 63 and an opening interval 64 of the second chopper, and a difference 65 between the opening times of the second chopper and the first chopper are similar to the description of the second chopper in the fourth embodiment. An operation time period 69 of the measurement of the secondary ion by the mass spectrometer means a time difference between a measurement start time 70 at which the measurement is turned ON from OFF and a measurement finishing time 71 at which the measurement is turned OFF from ON. In the present embodiment, the operation time period 69 of the measurement of the secondary ion by the mass spectrometer is shorter than the opening interval 64 of the second chopper. Incidentally, the measurement time period 69 of the secondary ion by the mass spectrometer may be constant or may vary.

In examples illustrated in FIG. 6, the measurement start time 70 of the secondary ion by the mass spectrometer is the same time as an opening time 66 of the second chopper, but may not be particularly the same time, as long as the measurement time period 69 of the secondary ion by the mass spectrometer is shorter than the opening interval 64 of the second chopper. However, the measurement start time 70 of the secondary ion by the mass spectrometer can be the same time as the opening time 66 or a closing time 67 of the second chopper, from the viewpoint of controllability. In addition, there is the case where it is prevented that secondary ions to be measured by certain one time of the operation of measuring the secondary ions becomes contaminated with the secondary ions generated by the previous irradiation with the ion group, by controlling the measurement start time 70 of the secondary ions by the mass spectrometer so as to be later than the opening time 66 of the second chopper, and consequently the accuracy of the analysis is enhanced.

The measurement finishing time 71 of the secondary ion by the mass spectrometer is not limited in particular, as long as the measurement time period 69 of the secondary ion by the mass spectrometer is shorter than the opening interval 64 of the second chopper. When the measurement start time 70 of the secondary ion by the mass spectrometer is the same time as the closing time 67 of the second chopper, for instance, the controllability of the measurement finishing time 71 of the secondary ion becomes adequate by using the start time of the chopper in the next chopping operation. In addition, there is the case where it is prevented that a secondary ion to be measured by certain one time of the operation of measuring the secondary ion becomes contaminated with the secondary ion generated by the next irradiation with the ion group, by controlling the measurement finishing time 71 of the secondary ion by the mass spectrometer so as to be earlier than the opening time of the next chopping operation by the second chopper, and consequently the accuracy of the analysis is enhanced.

Other parts of the constitution are similar to those in Embodiment 4.

Eighth Embodiment

In the device of the present embodiment, as is illustrated in FIG. 7, a time-of-flight mass separator 72 is used as an ion separator which is arranged between the above described first chopper 41 and second chopper 42.

The time-of-flight mass separator has high mass resolution. In addition, when the time-of-flight mass separator is used, a parameter which should be controlled so that the ion is separated into the ion group becomes only a time difference, and accordingly the simplicity and the accuracy of the control are enhanced. By the above operation, in the device of the present embodiment, the ion group having the high mass resolution and high mass accuracy can be simply obtained.

An operation of the device of the present embodiment illustrated in FIG. 7 will be described below. A first ion group is selected from an aggregate of ions which contains ions that have been released from the ion source and have various masses, and has a wide time period width, by a chopping operation by the first chopper 41. The first ion group has a small time period width and contains ions having various masses. Next, the ions in the above described first ion group containing the ions having various masses fly at a speed corresponding to each mass-to-charge ratio, in the time-of-flight mass separator 72. Thereby, the ions in the first ion group are separated according to each of the mass-to-charge ratios, and become an aggregate of a plurality of ions, which mainly contains ions having a particular mass and has a long time period width. Incidentally, the plurality of ion groups has each a long time period width, and occasionally overlaps each other. Next, the second chopper 42 performs the chopping operation for a target ion group which mainly contains a target ion out of the aggregate of the plurality of ions. As a result, the ion group formed of ions which have short time period widths and have a desired mass is selected as the second ion group. By the above operation, the ion group which has a short time period width and has a desired average mass can be simply and accurately obtained. The ion group irradiation unit irradiates the sample with the second ion group.

The setting of a difference between the opening times of the first chopper and the second chopper is not limited in particular, and may be set randomly or may be set so as to suit a purpose. For instance, for the purpose of irradiating the sample with an ion having a particular mass, the second chopper may be operated so as to suit the time difference during which the ion having the mass passes between the first chopper and the second chopper.

Incidentally, a time period which the ions having the particular mass-to-charge ratio spend before reaching the second chopper after having passed through the first chopper can be calculated as a delay time period (flight time period). Specifically, a time period t during which the ion that has a mass m and has a number z of electric charges and flies due to an accelerating voltage V flies through a flight path length having a whole length L at an equal speed can be determined from Expression (1). In Expression (1), e represents an elementary charge.

$$t = L(m/2zeV)^{1/2} \quad \text{Expression (1)}$$

When the flight path length L is defined as a length of the time-of-flight mass separator or a distance between the first chopper and the second chopper (when time-of-flight mass separator is not arranged separately from lens barrel of device, and potential based on ground potential is provided), a difference between the opening times of the first and second choppers for passing ions having a particular mass can be determined by the application of Expression (1). Incidentally, as the flight path length is longer, the mass resolution is more enhanced, but the flight path length of approximately 0.1 to 1 m can be used in consideration of the balance with the restriction on the throughput and the space.

The opened time period of the first chopper is not limited in particular, but the time period generally within a range of 0.5 nsec to 50 μsec is used. The opened time period of the chopper exerts an influence on the mass resolution in a time-of-flight mass separator which will be described later, and accordingly may be determined in consideration of the balance between various parameters such as the fight distance length and the accelerating voltage and a desired mass resolution of primary ions.

The opened time period of the second chopper is not limited in particular, but the time period generally within a range of 0.5 nsec to 50 μsec is used. However, there is the case where the opened time period exerts an influence on the mass resolution of the secondary ions which are emitted from the sample that has been irradiated with the primary ions. Specifically, there is the case where when the time period width of the ion group of the primary ion is excessively long, uncertainty of the generating time of the secondary ion increases and the mass resolution is lowered. On the other hand, as the mass-to-charge ratio of the primary ion is larger, the time period which the primary ion spends before passing through the second chopper becomes long. Accordingly, the opened time period shall be set to be large. The above described opened time period may be determined in consideration of these balances.

Other parts of the constitution are similar to those in Embodiment 4.

Ninth Embodiment

In the present embodiment, a time-of-flight type mass spectrometer is used as the mass spectrometer which measures the secondary ions generated from the sample.

The time-of-flight type mass spectrometer guides all the secondary ions generated from the sample to a drawing electrode and accelerates the drawn secondary ions by an accelerating voltage V, then makes the secondary ions fly in a free space having the flight path length L, and makes the secondary ions reach a detector. The secondary ions are separated according to each of the mass-to-charge ratios, and accordingly if a time period t is measured which the secondary ions spend before reaching the detector, a mass m of each of the secondary ions can be determined based on Expression (1).

The time-of-flight type mass spectrometer enables high sensitivity analysis because of having a high transmittance of the ions, has high mass resolution and facilitates the separation between the peaks. Accordingly, the ascription of the peak and the identification of the molecule in the sample can be easily performed. In addition, the time-of-flight type mass spectrometer has a quick scan speed, and accordingly can be suitably used also from the viewpoint of shortening the measurement time period.

Other parts of the constitution are similar to those in Embodiment 1.

Tenth Embodiment

In the present embodiment, the mass spectrometer that measures the secondary ions is provided with a detector having a function of two-dimensionally detecting ions, which detects the secondary ions generated on the surface of the sample in a state of having kept a positional relationship at a position at which the secondary ions have been generated.

When the mass spectrometer provided with the detector having the function of two-dimensionally detecting ions is used, scanning by the primary ions becomes unnecessary, because the mass spectrometer can record the position on the surface of the sample, at which the secondary ions are generated. For this reason, the secondary ions at each of the positions in the target region can be collectively detected by simultaneous irradiation with the primary ions onto the target region on the sample. As a result, the measurement can be completed in a short time period, compared to the case where the sample is scanned with the primary ions.

The mass spectrometer in the present embodiment may have a projection adjusting electrode for adjusting a projection magnification, in addition to the drawing electrode, the mass separating portion and the above described detector. The projection adjusting electrode has a function of expanding or reducing the spatial distribution of the secondary ions, onto a two-dimensional plane perpendicular to a traveling direction of the secondary ions which move toward the detector.

The secondary ions generated on the surface of the sample by irradiation with the ion groups are drawn by the drawing electrode to which voltage of several to several tens kV is applied. Next, the drawn secondary ions are expanded or reduced to an arbitrary projection magnification by the projection adjusting electrode, and are guided into the mass separating portion. Next, the guided secondary ions are separated based on the mass-to-charge ratio, and are further expanded or reduced as needed. In the above processes, the relative positional relationship on the surface of the sample among the secondary ions is kept. The separated secondary ions are sequentially detected by the detector, and the mass information and the two-dimensional positional information are recorded.

A mass separation method by the mass spectrometer in the present embodiment is not limited in particular, but for instance, when the time-of-flight type of mass separation method is used, the detecting time period of the secondary ion (corresponding to mass of secondary ion) and the detected position of the secondary ion can be simultaneously recorded.

The type of detector having a function of two-dimensionally detecting ions is not limited, and the detector may have any structure as long as the detector can detect the time at which the ions are detected and can detect the position. For instance, any one of combinations can be used which include: a combination of MCP (microchannel plate) and a two-dimensional type of electron position detector (for instance, delay line detector); a combination of the MCP and a fluorescent plate; a combination of the MCP and a CCD (charge-coupled element) type two-dimensional detector; and a detector which has microscopic MCPs arranged in a two-dimensional shape therein.

When the secondary ions are measured with the use of the mass spectrometer in the present embodiment, the ion groups irradiate the sample with the projection type, and the secondary ions generated from the whole or a part of a region to be irradiated are measured. The position and area to be irradiated with the ion groups can be arbitrarily determined with the use of the primary ion irradiation device, based on the quantity of an ionic current, an incident angle, a distance between the surface of the sample and the ion irradiation unit, and the like. The area and the projection magnification of a target measurement region of the secondary ion can be arbitrarily determined with the use of a distance between the drawing electrode and the sample, a voltage applied to the drawing electrode, a voltage applied to a projection adjusting electrode, and the like.

When the secondary ion is measured with the use of the mass spectrometer in the present embodiment, the measurement of the secondary ion may be performed continuously or discretely per one irradiation with the ion group. When the measurement is performed discretely, the measurement timing is controlled according to the mass information on the target molecule, and thereby the mass distribution image of the target molecules can be obtained at a high speed.

Incidentally, the operation time period and the operation cycle of the chopper can be changed according to the type and the response state of the detector.

Other parts of the constitution are similar to those in Embodiment 9.

Eleventh Embodiment

In the present embodiment, the same time as a timing of the chopping operation (opening time or closing time) by a chopper or the time which has been delayed by a fixed time period after the timing is used as the measurement start time of the above described time-of-flight type mass spectrometer.

In the present embodiment, the measurement start time of the time-of-flight type mass spectrometer is not limited in particular. However, when irradiation with the ion group is repeated two or more times, and the measurement operation by the time-of-flight type mass spectrometer is performed for the irradiation with each of the ion groups, the measurement operation can be simplified and the control is facilitated by using the same time as the timing of the chopping operation by the chopper or the time which has been delayed by the fixed time period after the timing.

In addition, data processing is simplified by the present embodiment. A mass axis in the mass spectrum of the secondary ions, which is obtained by the mass spectrometer, usually deviates slightly from a true value. The deviation of the mass axis in the time-of-flight type mass spectrometer reflects the deviation among the flight start times of the secondary ions. Because of this, the time-of-flight type mass spectrometer is interlocked with the chopper, and a difference between the operation timing of the chopper and the measurement start time of the secondary ion is controlled to be constant. Thereby, even when the analysis cycle formed from the irradiation with the primary ion and the measurement of the secondary ion is repeated, the data can be obtained in which the above described deviation of the mass axis is equal every time. Because of this, data processing such as integration and calibration can be simply performed.

Incidentally, when there are a plurality of choppers, any one of choppers is selected and is interlocked with the measurement operation of the time-of-flight type mass spectrometer.

Other parts of the constitution are similar to those in Embodiment 9.

Twelfth Embodiment

In the present embodiment, the chopper includes a chopper which is formed of a combination of a deflecting electrode with an opening. The deflecting electrode means an electrode which is formed of at least two electrodes that are arranged in a direction different from a traveling direction of ions, and has a function of bending the traveling direction of the ions by a potential difference applied between the electrodes. The opening means a microscopic hole which passes ions in a direction toward a sample from an ion source (hereinafter referred to as downstream side as well) therethrough. The opening is arranged in the downstream side of the deflecting electrode. When the ions travel straight toward the opening, the deflecting electrode to which the voltage is applied bends the trajectory of the ions and guides the ions to the outer part of the opening, and thereby can intercept the ions for a fixed time period. On the contrary, when the application of the voltage to the deflecting electrode is stopped, the trajectory of the ions is returned to a straight direction, and the ions pass through the opening. Thereby, the ions can pass through the opening for a fixed time period. By the above operations, the chopper can select one part out of an aggregate of ions which have been generated from the ion source and have a wide time period width, as an ion group having a short time period width. A combination of the deflecting electrode with the opening facilitates the timing control of the chopping operation and is excellent in convergence properties of the ions, and accordingly can often be used.

The shape of the deflecting electrode is not limited in particular, but the electrode is used which has a length of approximately 10 to 200 mm along a direction along which the ions pass. The shape of the opening is not limited in particular, but an opening can be used of which the opening part is a circle shape and has a diameter of approximately 0.05 to 10 mm. The distance between the deflecting electrode and the opening is not limited in particular, but a distance of approximately 5 to 100 mm is used.

(a) to (c) of FIG. 8 illustrate examples of: a timing chart of the jet by an intermittent valve; a timing chart of the application of voltage to a first deflecting electrode; and a timing chart of the application of voltage to a second deflecting electrode, respectively, when the ion group selecting unit has a first chopper positioned in an upstream side, a second chopper positioned in a downstream side, and a time-of-flight mass separator arranged between the first and second choppers. Incidentally, the deflecting electrode in the first chopper is referred to as a first deflecting electrode, and the deflecting electrode in the second chopper is referred to as a second deflecting electrode. In addition, the opening in the first chopper is referred to as a first opening, and the opening in the second chopper is referred to as a second opening. Incidentally, the first opening and the second opening shall be arranged on the same axis.

An opened time period 74 and an opening interval 75 of the intermittent valve are similar to those in the first embodiment. An aggregate of neutral particles containing neutral cluster molecules which have been generated by the jet of the intermittent valve is ionized, and is formed into an aggregate of ions which contain cluster ions having various masses and have a wide time period width. When a voltage is applied (ON) to the first deflecting electrode, the aggregate of the ions is bent from the straight direction and collides with the outer parts of the opening, and thereby is intercepted. When the voltage which has been applied to the first deflecting electrode is turned OFF, a part of the aggregate of the ions passes through the first deflecting electrode, after a time difference 79 between the opening times of the chopper and the intermittent valve. After a time period 77 during which the voltage to the first deflecting electrode is stopped, the voltage is turned ON again, and thereby a part of the aggregate of the ions is intercepted again. By the operations of the voltage application ON/OFF/ON to the first deflecting electrode, only ions which have passed through the first deflecting electrode and have passed through the subsequent first opening during the time period 77 are selected as a first ion group. The first ion group contains ions which have a small time period width and various masses. Next, the first ion group flies in the time-of-flight mass separator, is separated into ions according to each of the masses in the process, and reaches the second deflecting electrode at different times according to each of the masses. In the second deflecting electrode as well as in the first deflecting electrode, when the voltage application is turned ON, the ions are bent from the straight direction and are intercepted, in a similar way to the first deflecting electrode. Because of this, by an operation of turning the voltage application to the second deflecting electrode OFF, after a time difference 83 between the opening times of the chopper and the intermittent valve, and turning the voltage application ON again after a time period 81 during which the voltage application to the second deflecting electrode has been stopped, an ion group which mainly contains a cluster ion having a particular mass and has a short time period width can be selected from the first ion group, as the second ion group. An ion group irradiation unit irradiates the sample with the second ion group. By an operation of performing the combination of an ion group selecting operation (voltage application OFF) which is performed by the above described first deflecting electrode and the chopper in a time period interval 78 with an ion group selecting operation (voltage application OFF) which is performed by the second deflecting electrode and the chopper in a time period interval 82 two or more times per one jet by the intermittent valve, the irradiation with the ion group onto the sample can be performed in a short time cycle.

The voltage application of ON/OFF to the deflecting electrode can be accurately performed with the use of a waveform generator. In addition, it is also possible to branch a voltage application signal to be sent to the deflecting electrode, and to send the above described branched signal to a mass spectrometer as a trigger signal, at the same time or at the delayed time by a fixed time period through a delay time generating apparatus. In this case, the chopping operation by the chopper can be accurately interlocked with the measurement of the secondary ion by the mass spectrometer.

Other parts of the constitution are similar to those in Embodiment 1.

Thirteenth Embodiment

In the present embodiment, an ion material of a cluster ion contained in the ion group contains any one of a gas, a non-metallic liquid and a mixture of a gas and a non-metallic liquid at normal temperatures and normal pressures. In the present embodiment, the kind of material of the ion is not limited in particular, but a cluster ion having a larger cluster size is generated more easily at the time when the gas or the non-metallic liquid is used as the material of the ion than the time when the liquid metal is used. As the cluster size is larger, the yield of the secondary ion is more enhanced. As a result, the repeat count necessary for obtaining sufficient intensity can be reduced, and the analysis can be finished in a short time period. For this reason, the material of the ion can include any one of the gas, the non-metallic liquid and the mixture of the gas and the non-metallic liquid at the normal temperatures and normal pressures.

Gases at the normal temperatures and normal pressures include a noble gas such as argon and xenon, and oxygen. However, the present embodiment is not limited to these gases.

Non-metallic liquids at the normal temperatures and normal pressures include water, acid, alkali and an organic solvent such as alcohol. However, the present embodiment is not limited to these non-metallic liquids.

Other parts of the constitution are similar to those in Embodiment 1.

Fourteenth Embodiment

In the present embodiment, a cluster ion contained in an ion group contains at least one kind of molecule out of water, acid and alcohol. In the present embodiment, a constituent atom species or a constituent molecule species of an ion which constitutes the cluster ion group is not limited in particular, but when a primary ion containing at least one kind of molecule out of water, acid and alcohol irradiates a sample, the generation of protonated ion can be promoted with respect to a molecule having a proton affinity such as a biomolecule. As a result, the detection sensitivity to a precursor ion of the above described molecule is enhanced. For this reason, the cluster ion contained in the ion group can contain a molecule which includes at least one kind out of water, acid and alcohol.

The ion containing the water is not limited in particular, but suitable examples of the ion include $[(H_2O)_n]^+$; (n=1 to 100,000), and $[(H_2O)n+mH]^{m+}$ (n=1 to 100,000 and m=1 to 100,000).

An example will be described below in which an ion group is used that is formed of a water cluster ion ($[(H_2O)_{1,000\pm20}]^+$) which contains 1,000±20 water molecules. Incidentally, ($[(H_2O)_{1,000\pm20}]^+$) means an ion obtained from such a result that an error of ±20 molecules occurs when the cluster ion is selected as the ion group, though the average number of the water molecules contained in the cluster ion is 1,000 molecules.

The water cluster ion can be obtained by operations of using water as the material of the ion, jetting the water which has been heated in the ion material supply unit into a vacuum by the intermittent valve, and ionizing a formed neutral water cluster by the electron bombardment ionization method. A part of an aggregate of a plurality of ions which are generated by the ionization of the material that has been jetted once by the intermittent valve, and have a size of the cluster, is selected by the first chopper as a first ion group. The above described first ion group is subjected to mass separation in the time-of-flight mass separator, and is subjected to a chopping operation by a second chopper after a particular time period ΔT1 has passed after the chopping operation by the first chopper. Then the second ion group is selected which is formed of $[(H_2O)_{1,000\pm20}]^+$. The sample containing the biomolecule is irradiated with the selected second ion group formed of $[(H_2O)_{1,000\pm20}]^+$. The secondary ion emitted from the irradiated surface is subjected to mass spectrometry by the time-of-flight type mass spectrometer during a measurement time period Δt1. Next, the above described ion selecting, irradiation with the ions and measurement of the secondary ion are repeated further one or more times before the intermittent valve performs the next jet. By the above operations, the mass spectrum of the secondary ions having sufficient intensity for the biological sample can be obtained in a short time period. However, the present embodiment is not limited to the above described example.

The kind of acid is not limited in particular, but examples of the acid can include formic acid, acetic acid and trifluoroacetic acid.

The kind of alcohol is not limited in particular, but examples of the alcohol can include methanol, ethanol and isopropyl alcohol.

The number and the ratio of the molecules of water, acid and alcohol, which are contained in the ion group, are not limited in particular. However, as the number of the above described molecules is larger, the protonation rate is occasionally enhanced.

Other parts of the constitution are similar to those in Embodiment 13.

Fifteenth Embodiment

In the present embodiment, the cluster ion contained in the ion group contains a rare gas molecule. In the present embodiment, a constituent atom species or a constituent molecule species of an ion which constitutes the ion group is not limited in particular, but when a primary ion containing the molecule of the noble gas irradiates a sample, the contamination on the surface of the sample due to irradiation with the primary ion can be reduced because the reactivity of the molecule of the noble gas is low. Because of this, the cluster ion contained in the ion group can include the molecule of the noble gas.

The kind of molecule of the noble gas is not limited in particular, but argon or xenon can be used from the viewpoint of the mass and the cost.

Other parts of the constitution are similar to those in Embodiment 13.

Sixteenth Embodiment

In the present embodiment, the fluctuation of an ionic current value or a cluster size of an irradiating ion group is monitored, the result is fed back to a setting condition of a device, and the above described fluctuation is reduced.

When the selecting of the ion group and the irradiation with the ion group are performed over a long time period, even though the setting condition of the device is the same within the time period, there is the case where the electric current value or the cluster size of the ion group varies. In this case, the measurement results vary and cause dispersion according to each cycle in which the irradiation with the ion group and the measurement of the secondary ion are repeated, and accordingly the analysis accuracy and the reproducibility are lowered. Accordingly, the above described fluctuation can be reduced by being monitored and being fed back to the setting condition of the device.

The ionic current value or the cluster size of the ion group can be obtained by direct measurement. In this case, the mass spectrum is acquired by an operation of irradiating an MCP installed in the device with the ion group. The ionic current value is obtained from the peak area value of the mass spectrum, and the cluster size is obtained from the mass and the half-value width in the peak. The ionic current value and the cluster size are sampled periodically while the sample is irradiated with the ion group over a long time period with the use of the above methods, and thereby the fluctuation can be monitored.

In addition, the ionic current value of the ion group can be obtained also by calculation from the electric current value of the continuous ion beam at the time before the ions are selected as the ion group. In this case, firstly, a sample holding mechanism or another portion in the device is irradiated with the continuous ion beam, and the electric current value is measured. Furthermore, a Faraday cup contained in the sample holding mechanism can be irradiated with the continuous ion beam, and the electric current value can be measured. Next, the ionic current value of the ion group is calculated with the use of the measured electric current value and a duty ratio (time period width of ion group/start time interval of chopping operation which selects ion group) which is set when the ion group is selected from the continuous ion beam. The ionic current value is periodically sampled while the sample is irradiated with the ion group over a long time period, with the use of the above methods, and thereby the fluctuation can be monitored.

Furthermore, the fluctuation of the ionic current value or the cluster size of the ion group can be determined also from the total amount of the secondary ions generated from the surface of the sample which is irradiated with the ion group. When the ionic current value is small, the total amount of the secondary ions also decreases. In addition, even though the ionic current values are equal, when the cluster size becomes small, the sputtering efficiency is lowered. Accordingly, the total amount of the secondary ions also decreases. Accordingly, the fluctuation of the ionic current value and the cluster size can be monitored by the operation of measuring the total amount of the secondary ions, which is obtained in each cycle in which the irradiation with the ion group and the measurement of the secondary ion are repeated, by the mass spectrometer, while a sample is irradiated with the ion group over a long time period.

An object to be monitored may be the ionic current value, may also be the cluster size, or may be even both of them.

The monitored result is fed back to the setting condition of the ion group irradiation device, and the setting condition is adjusted. As for the setting conditions, an initial value of the ionic current value or the cluster size in an initial period of the irradiation with the ion or the total amount of the secondary ions generated from the surface of the sample which is irradiated with the ion group may be adjusted, based on any one of the initial value when the irradiation with the ion group has been started, the average value while the sample is irradiated with the ion group, and a value which has been monitored on one cycle prior to a cycle of being monitored. Alternatively, the setting conditions may be adjusted based on the set value of the ionic current value or the cluster size, which is determined by the setting condition.

The setting conditions which are adjusted by the feedback are not limited in particular. However, the fluctuation of the ionic current value or the cluster size originates mainly in the fluctuation of a pressure at which the material of the ion is jetted by the intermittent valve. Because of this, examples of the setting conditions which are adjusted by the feedback include a pressure at which the material of the ion is supplied to the intermittent valve, a pressure in the vicinity of the intermittent valve, and a time period width and an operation time interval of the intermittent valve. In addition to those, the operation time intervals of the intermittent valve and the chopper, and the time period width and the operation time interval of the chopper may be adjusted. In addition to those, a distance between the intermittent valve and the ionization unit may be adjusted. In addition to those, voltages may be adjusted which are each applied to the intermittent valve, the ionization unit, the chopper, the ion separator and the like. In addition to those, the number of the irradiation times with the ion group may be adjusted.

The monitoring of the fluctuation of the ionic current value and the cluster size, and the adjustment of various setting conditions according to the feedback may be manually performed by a measuring person, or may also be automatically performed by a device.

Other parts of the constitution are similar to those in Embodiment 1.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-131637, filed Jun. 24, 2013, which is hereby incorporated by reference herein in its entirety.

What is claimed is:

1. An ion group irradiation device comprising:
   an ion source which generates an ion; and
   an ion group selecting unit which selects an ion group including a cluster ion from ions released from the ion source, in an ion group irradiation device for irradiating a sample with the ion group, wherein
   the ion source has a pressure gradient forming unit for changing a pressure with which a material of the cluster ion is jetted, with time,
   the ion group selecting unit has a chopper which performs a chopping operation of selecting the ion group by passing and blocking the cluster ions in a traveling direction by the opening and closing of the chopper, and
   the chopper performs two or more times of the chopping operations per one time of a pressure gradient forming operation by the pressure gradient forming unit.

2. The ion group irradiation device according to claim 1, wherein the pressure gradient forming unit includes an intermittent valve which intermittently jets the material of the cluster ion.

3. The ion group irradiation device according to claim 1, wherein the ion group selecting unit has a first chopper that is positioned on an ion source side, a second chopper, and an ion separator arranged between the first and second choppers, and at least the first chopper performs two or more times of the chopping operations per one time of the pressure gradient forming operation by the pressure gradient forming unit.

4. The ion group irradiation device according to claim 3, wherein the second chopper opens simultaneously with an opening time or a closing time of the first chopper, or opens later than the times by a fixed time period.

5. The ion group irradiation device according to claim 1, wherein the ion separator is a time-of-flight mass separator.

6. The ion group irradiation device according to claim 1, wherein the chopper includes a chopper which is formed of a combination of a deflecting electrode and an opening.

7. The ion group irradiation device according to claim 1, wherein an ion material of the cluster ion contained in the ion group contains one of a gas, a non-metallic liquid and a mixture of a gas and a non-metallic liquid at normal temperatures and normal pressures.

8. The ion group irradiation device according to claim 1, wherein the cluster ion contained in the ion group contains at least one kind of molecule out of water, acid and alcohol.

9. The ion irradiation device according to claim 7, wherein the cluster ion contained in the ion group contains a rare gas molecule.

10. A secondary ion mass spectrometer comprising:
the ion irradiation device according to claim 1; and
a mass spectrometer which measures a mass of a secondary ion generated from a sample which has been irradiated with an ion group due to the ion irradiation device.

11. The secondary ion mass spectrometer according to claim 10, wherein the mass spectrometer uses any of times out of an opening time and a closing time of the chopper, and a time which has been delayed by a fixed time period after the times, as a measurement start time of the secondary ion.

12. The secondary ion mass spectrometer according to claim 10, wherein the measurement time period of the secondary ion by the mass spectrometer is shorter than an interval between a time when the chopper opens and a time when the chopper opens next time.

13. The secondary ion mass spectrometer according to claim 10, wherein
the ion group irradiation device has a first chopper that is positioned on an ion source side, a second chopper, and an ion separator arranged between the first and second choppers, and
the mass spectrometer uses any of times out of an opening time or a closing time of the chopper, and a time which has been delayed by a fixed time period after the times, as a measurement start time of the secondary ion.

14. The secondary ion mass spectrometer according to claim 13, wherein the measurement time period of the secondary ion by the mass spectrometer is shorter than an interval between a time when the second chopper opens and a time when the second chopper opens next time.

15. The secondary ion mass spectrometer according to claim 10, wherein the mass spectrometer is a time-of-flight type mass spectrometer.

16. The secondary ion mass spectrometer according to claim 10, wherein the mass spectrometer is provided with a detector having a function of two-dimensionally detecting ions, which detects the secondary ion generated on a surface of the sample in a state of having kept a positional relationship at a position at which the secondary ion is generated.

17. A secondary ion mass spectrometry method comprising obtaining a mass spectrum or a mass distribution image of secondary ions of a sample by using the secondary ion mass spectrometer according to claim 10.

* * * * *